(12) United States Patent
Kurahashi et al.

(10) Patent No.: US 9,380,785 B2
(45) Date of Patent: Jul. 5, 2016

(54) ANTIVIRAL RESIN MEMBER

(75) Inventors: Shinji Kurahashi, Tokyo (JP); Nobukazu Motojima, Tokyo (JP); Yoko Fukui, Tokyo (JP); Tsuruo Nakayama, Tokyo (JP)

(73) Assignee: NBC MESHTEC, INC., Tokyo (JP)

(*) Notice: Subject to any disclaimer, the term of this patent is extended or adjusted under 35 U.S.C. 154(b) by 0 days.

(21) Appl. No.: 14/127,709

(22) PCT Filed: Jul. 6, 2012

(86) PCT No.: PCT/JP2012/004395
§ 371 (c)(1),
(2), (4) Date: Dec. 19, 2013

(87) PCT Pub. No.: WO2013/005446
PCT Pub. Date: Jan. 10, 2013

(65) Prior Publication Data
US 2014/0127321 A1  May 8, 2014

(30) Foreign Application Priority Data
Jul. 6, 2011 (JP) ................................ 2011-150381

(51) Int. Cl.
| | | |
|---|---|---|
| A01N 59/20 | (2006.01) | |
| B29C 55/00 | (2006.01) | |
| C08K 3/00 | (2006.01) | |
| C08K 5/17 | (2006.01) | |
| C08L 101/00 | (2006.01) | |
| A01N 25/10 | (2006.01) | |
| A01N 59/16 | (2006.01) | |
| B29C 35/00 | (2006.01) | |
| C08J 3/22 | (2006.01) | |
| C08J 5/18 | (2006.01) | |
| C08K 3/16 | (2006.01) | |
| B29C 55/06 | (2006.01) | |
| B29C 55/12 | (2006.01) | |

(52) U.S. Cl.
CPC ............... *A01N 59/20* (2013.01); *A01N 25/10* (2013.01); *A01N 59/16* (2013.01); *B29C 35/00* (2013.01); *B29C 55/00* (2013.01); *C08J 3/22* (2013.01); *C08J 5/18* (2013.01); *C08K 3/00* (2013.01); *C08K 3/16* (2013.01); *C08K 5/17* (2013.01); *C08L 101/00* (2013.01); *B29C 55/06* (2013.01); *B29C 55/12* (2013.01); *C08J 2323/06* (2013.01)

(58) Field of Classification Search
CPC ........ A01N 59/16; A01N 59/20; B29C 55/00; B29C 55/06; B29C 55/12; C08K 3/00; C08K 5/17; C08L 101/00
See application file for complete search history.

(56) References Cited

U.S. PATENT DOCUMENTS

| | | | |
|---|---|---|---|
| 6,497,868 B1 * | 12/2002 | Tanahashi | ................... 424/78.08 |
| 8,585,753 B2 * | 11/2013 | Scanlon et al. | .............. 623/1.42 |
| 2003/0211035 A1 | 11/2003 | Burns et al. | |
| 2008/0057135 A1 * | 3/2008 | Allen | ...................... A01N 59/16 424/618 |
| 2011/0195108 A1 * | 8/2011 | Fujimori et al. | .............. 424/443 |

FOREIGN PATENT DOCUMENTS

| | | |
|---|---|---|
| CN | 1303599 | 7/2001 |
| JP | 11-99200 | 4/1999 |
| JP | 2007-513959 | 5/2007 |
| JP | 2009-523890 | 6/2009 |
| JP | 2010-30984 | 2/2010 |
| JP | 2010-84050 | 4/2010 |
| JP | 4584339 | 9/2010 |
| JP | 2010-275196 | 12/2010 |
| JP | 2012-24566 | 2/2012 |
| JP | 2012-71040 | 4/2012 |
| JP | 2012-72100 | 4/2012 |
| WO | 01/35924 | 5/2001 |
| WO | 2005/074947 | 8/2005 |
| WO | 2007/084452 | 7/2007 |
| WO | 2010/026730 | 3/2010 |
| WO | 2010/067873 | 6/2010 |
| WO | 2010/126173 | 11/2010 |

OTHER PUBLICATIONS

International Search Report issued Oct. 2, 2012 in International (PCT) Application No. PCT/JP2012/004395.
International Preliminary Report on Patentability issued Jan. 7, 2014 and English translation of Written Opinion of the International Searching Authority issued Oct. 2, 2012 in International (PCT) Application No. PCT/JP2012/004395.
Extended European Search Report issued Nov. 4, 2014 in corresponding European Patent Application No. 12808121.3.
Entsiklopediya polimerov [Encyclopedia of polymers] v.2, 1974, Sovetskaya Entsiklopediya.

* cited by examiner

*Primary Examiner* — Suzanne Ziska
(74) *Attorney, Agent, or Firm* — Wenderoth, Lind & Ponack, L.L.P.

(57) ABSTRACT

To provide an antiviral resin member which can efficiently inactivate viruses and has excellent sustainability.
An antiviral resin member comprising a resin, an antiviral agent, and a surface potential-controlling agent, characterized in that the surface potential-controlling agent causes the surface potential of the antiviral resin member to shift to a value on the positive side of the potential of the resin alone.

4 Claims, 2 Drawing Sheets

ANTIVIRAL RESIN MEMBER

TECHNICAL FIELD

The present invention relates to a resin member that can inactivate viruses, and particularly, to an antiviral resin member that can inactivate various attached viruses even in the presence of a lipid or a protein regardless of the presence of an envelope.

BACKGROUND ART

Recently, deaths that are caused by infection of viruses such as severe acute respiratory syndrome (SARS), a norovirus, and an avian influenza virus have been reported. Currently, the world faces the risk of a "pandemic" in which viral infection spreads throughout the world due to developments in transportation and the mutations of viruses. In addition, severe suffering due to novel influenza or foot-and-mouth disease is also caused, and an urgent countermeasure is required. In order to deal with such a situation, the development of an antiviral agent based on a vaccine is hastened. However, since a vaccine has specificity, an infection that can be prevented by the vaccine is restricted to a specific viral infection.

At hospitals or medical clinics, methicillin-resistant *staphylococcus aureus* (MRSA) is brought into the hospital or the medical clinic by a carrier or an infected person, or a species is mutated from *Staphylococcus aureus* to MRSA by antibiotic administration. From a patient directly or via a health professional or an environment including a used article such as a medical coat, a pajama, a sheet, and gloves and a facility such as a wall and an air conditioner, another patient and health professional may be immediately infected with such bacteria. Such hospital infection is a serious problem in society. Therefore, there is a strong demand for the development of an antiviral member that can exhibit effective antibacterial and antiviral effects against various bacteria and viruses.

In order to solve the problems, Patent Literature 1 has proposed a method for applying an antibacterial film or an antibacterial substance to the surface of a medical apparatus. Patent Literature 2 has proposed a fiber containing an antiviral substance and a fibrous structure containing an antiviral fiber.

CITATION LIST

Patent Literature

Patent Literature 1: Japanese Translation of PCT Application Publication No. 2009-523890
Patent Literature 2: Japanese Patent No. 4584339

SUMMARY OF INVENTION

Technical Problem

A mask in Patent Literature 1 shows an effect against bacteria such as *Escherichia coli*. However, Patent Literature 1 does not describe embodiments concerning viruses. Therefore, it is not clear that the mask has an action of inactivating viruses.

The antiviral fibrous structure in Patent Literature 2 can be applied to a fibrous cloth. However, it is not clear that the antiviral fibrous structure can be applied to a film and a sheet that do not contain fibers and a molded body.

The present invention has been made to solve the conventional problems. It is an object of the present invention to provide an antiviral resin member that can effectively inactivate viruses and has excellent sustainability.

Solution to Problem

A first aspect of the present invention provides an antiviral resin member containing a resin, an antiviral agent, and a surface potential-controlling agent including a cationic surfactant, wherein the surface potential-controlling agent causes the surface potential of the antiviral resin member to shift to a value on the positive side of the surface potential of the resin alone.

A second aspect of the present invention provides the antiviral resin member according to the first aspect of the present invention, wherein the antiviral agent contains, as an active ingredient, iodide particles including iodine and at least one of elements of Groups 8 to 15 in the fourth to sixth periods of the periodic table.

A third aspect of the present invention provides the antiviral resin member according to the second aspect of the present invention, wherein the element of Groups 8 to 15 in the fourth to sixth periods of the periodic table is Cu, Ag, Sb, Ir, Ge, Sn, Tl, Pt, Pd, Bi, Au, Fe, Co, Ni, Zn, In, or Hg.

A fourth aspect of the present invention provides the antiviral resin member according to any one of the first to third aspects of the present invention, wherein the antiviral agent contains, as an active ingredient, particles of at least one kind of monovalent copper compound.

A fifth aspect of the present invention provides the antiviral resin member according to the forth aspect of the present invention, wherein the monovalent copper compound is a chloride, an acetate compound, a sulfide, an iodide, a bromide, a peroxide, an oxide, or a thiocyanide.

A sixth aspect of the present invention provides the antiviral member according to any one of the first to fifth aspects of the present invention, wherein the antiviral resin member is a molded body obtained by molding followed by heating and stretching.

A seventh aspect of the present invention is a method for producing an antiviral resin member including: forming a molded body from a resin, an antiviral agent, and a surface potential-controlling agent including a cationic surfactant, and heating and stretching the molded body.

Advantageous Effects of Invention

According to the present invention, an antiviral agent and a surface potential-controlling agent are contained in a resin to control the potential so that viruses are easy to adsorb to the surface of a resin member. Thus, the antiviral agent can effectively inactivate viruses. In particular, viruses having no envelope can be effectively inactivated by the presence of the surface potential-controlling agent. Furthermore, since the antiviral agent and the surface potential-controlling agent are contained in the resin, the antiviral agent is hard to be separated. Therefore, the present invention can provide an antiviral resin member that holds the virus inactivation effect for longer periods.

DESCRIPTION OF EMBODIMENTS

Hereinafter, an embodiment of the present invention will be described in detail with reference to FIG. 1.

Figure 1:
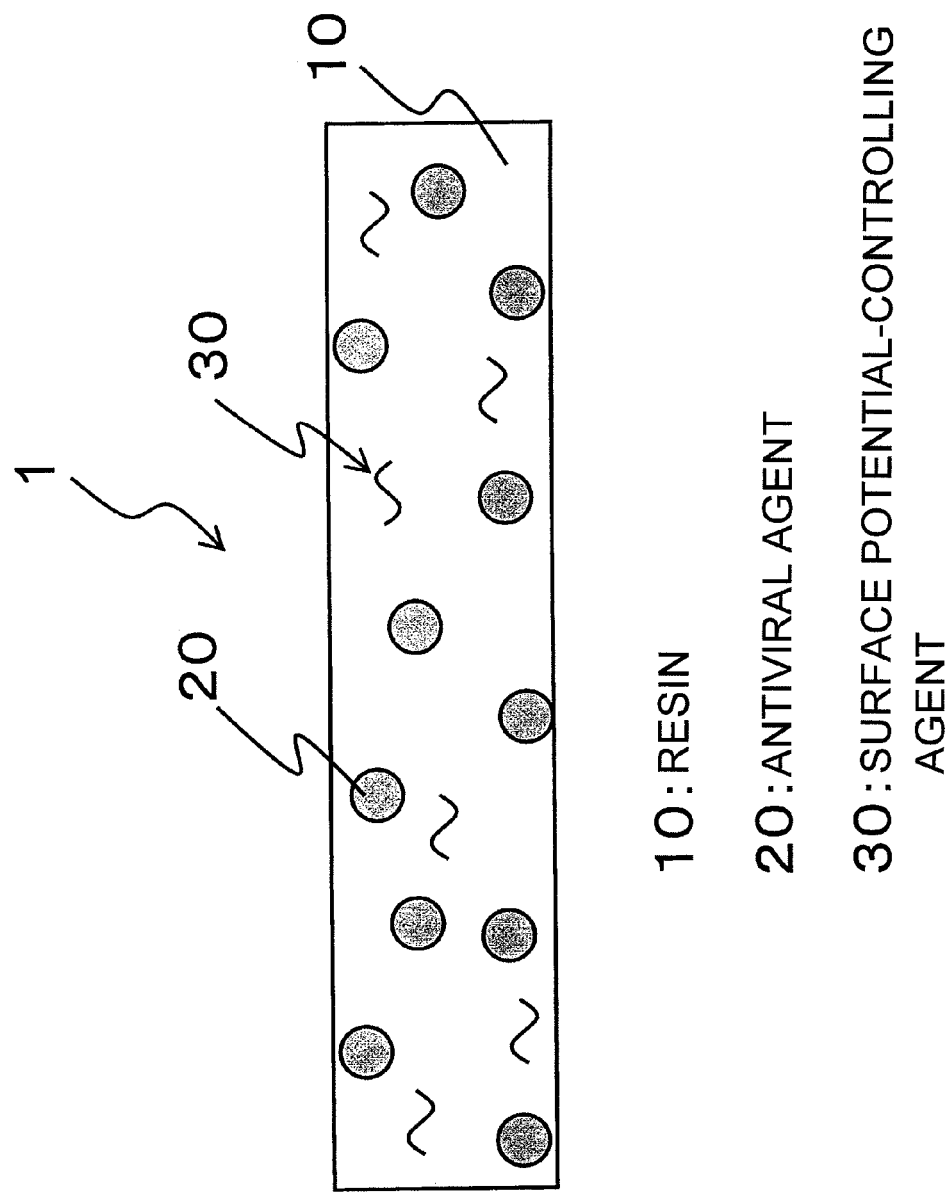
FIG. 1 is a schematic view of an antiviral resin member of the present embodiment.

FIG. 1 is a view schematically illustrating a portion of a cross section of an antiviral resin member 1 according to the embodiment of the present invention. The antiviral resin member 1 is configured to include a resin 10, an antiviral agent 20, and a surface potential-controlling agent 30. For example, as shown in FIG. 1, the antiviral resin member 1 may have a structure in which the antiviral agent 20 and the surface potential-controlling agent 30 are dispersed in the resin 10.

The resin 10 of the embodiment of the present invention is not particularly limited, and examples thereof may include a thermoplastic resin such as a polyethylene resin, a polypropylene resin, a polystyrene resin, an ABS resin, an AS resin, an EVA resin, a polymethylpentene resin, a polyvinyl chloride resin, a polyvinylidene chloride resin, a polymethyl acrylate resin, a polyvinyl acetate resin, a polyamide resin, a polyimide resin, a polycarbonate resin, a polyethylene terephthalate resin, a polybutylene terephthalate resin, a polyacetal resin, a polyarylate resin, and a polysulfone resin; a silicone resin; and a thermoplastic elastomer including a styrene-based elastomer such as a polystyrene elastomer, an olefin-based elastomer such as a polyethylene elastomer and a polypropylene elastomer, a polyurethane-based elastomer such as a polyurethane elastomer, a polyvinyl chloride-based elastomer, a polyester-based elastomer, and a nylon-based elastomer.

The antiviral agent 20 of the embodiment is not particularly limited as long as it is a substance capable of inactivating viruses. It is preferable that the antiviral agent 20 be monovalent copper compound fine particles and/or iodide fine particles. By using such fine particles, viruses can be inactivated regardless of the presence of an envelope.

Currently, a virus inactivation mechanism of virus inactivation fine particles is not completely clear, and is considered as follows. Virus inactivation fine particles come into contact with a moisture content in air or droplets. As a result, a portion of the virus inactivation fine particles is subjected to an oxidation-reduction reaction or generates an active species. This may affect electric charge at the surface of viruses attached to the antiviral resin member of the embodiment, DNA, or the like, to inactivate the viruses.

At least one kind of antiviral iodide in the embodiment includes iodine and an element of Groups 8 to 15 in the fourth to sixth periods of the periodic table. It is preferable that the element of Groups 8 to 15 in the fourth to sixth periods of the periodic table be Cu, Ag, Sb, Ir, Ge, Sn, Tl, Pt, Pd, Bi, Au, Fe, Co, Ni, Zn, In, or Hg. Furthermore, it is more preferable that iodide particles contained in the antiviral agent of the embodiment be particles of at least one selected from the group consisting of CuI, AgI, $SbI_3$, $IrI_4$, $GeI_4$, $GeI_2$, $SnI_2$, $SnI_4$, TlI, $PtI_2$, $PtI_4$, $PdI_2$, $BiI_3$, AuI, $AuI_3$, $FeI_2$, $CoI_2$, $NiI_2$, $ZnI_2$, HgI, and $InI_3$.

In contrast, it is preferable that an antiviral monovalent copper compound in the embodiment be a chloride, an acetate compound, a sulfide, an iodide, a bromide, a peroxide, an oxide, or a thiocyanide. Furthermore, it is more preferable that particles of the monovalent copper compound contained in the antiviral agent of the embodiment be particles of at least one selected from the group consisting of CuCl, $Cu(CH_3COO)$, CuBr, CuI, CuSCN, $Cu_2S$, and $Cu_2O$.

In the antiviral agent 20 of the embodiment, it is particularly preferable that the particles be particles of at least one selected from the group consisting of CuI, AgI, $SnI_4$, CuCl, CuBr, and CuSCN that have excellent storage stability in air among the iodide or monovalent copper compound particles.

A virus that can be inactivated by the antiviral agent of the embodiment is not particularly limited. Various viruses can be inactivated regardless of the genome type or the presence of an envelope. Examples thereof may include a rhinovirus, a poliovirus, a rotavirus, a foot-and-mouth disease virus, a norovirus, an enterovirus, a hepatovirus, an astrovirus, a sapovirus, a hepatitis E virus, influenza A, B, and C viruses, a parainfluenza virus, a mumps virus (*Myxovirus parotitidis*), a measles virus, a human metapneumovirus, an RS virus, a nipah virus, a Hendra virus, a yellow fever virus, a dengue virus, a Japanese encephalitis virus, a West Nile virus, hepatitis B and C viruses, Eastern and Western equine encephalitis viruses, an O'nyong-nyong virus, a rubella virus, a Lyssavirus, a Junin virus, a Machupo virus, a Guanarito virus, a Sabia virus, a Crimean-Congo hemorrhagic fever virus, a phlebotomus fever virus, a hantavirus, a Sin Nombre virus, a rabies virus, an Ebolavirus, a Marburg virus, a bat lyssavirus, a human T cell leukemia virus, a human immunodeficiency virus, a human coronavirus, a SARS coronavirus, a human parvovirus, a polyomavirus, a human papilloma virus, an adenovirus, a herpes virus, a varicellavirus, a Zoster virus, an EB virus, a cytomegalovirus, a smallpox virus, a monkeypox virus, a cowpox virus, a molluscipoxvirus, and a parapoxvirus.

In the embodiment, the particle diameter of the antiviral agent is not particularly limited and can be appropriately set by those skilled in the art. In consideration of a decrease in the strength of the resin member, it is preferable that the particle diameter of the antiviral agent be 3 µm or less. In the embodiment, the particle diameter is not particularly limited and can be appropriately set by those skilled in the art, but the particle diameter is preferably 1 nm or more from the viewpoints of production, handling properties, and chemical stability of the particles. An average particle diameter used herein is referred to as a volume-average particle diameter.

In the embodiment, the contained amount of the antiviral agent is not particularly limited and can be appropriately set by those skilled in the art. When the antiviral agent is contained in the entire resin member 1, it is preferable that the contained amount of the antiviral agent in the resin member 1 fall within a range of 0.5% by mass or more and 40% by mass or less. When the contained amount is less than 0.5% by mass, the effect of antiviral properties is low. When the antiviral agent is contained in an amount of 40% by mass or less, the antiviral properties are enough for practical use. When the amount exceeds 40% by mass, the strength of the resin member is decreased.

In the embodiment, the entire resin member or only a surface portion of the resin member may be filled with the antiviral agent. Therefore, only a portion that should exhibit an antiviral effect may be filled with the antiviral agent. For example, when the resin member has a film shape, a two-layered film may be adopted. In this structure, only a surface that is expected to exhibit the effect can be filled with the antiviral agent. Furthermore, the resin member may have a fibrous shape. When the resin member in the fibrous shape has a core-sheath structure, only a sheath portion can be filled with the antiviral agent. Accordingly, the content of the antiviral agent can be decreased. A high antiviral effect can be achieved while a decrease in the strength of the resin member is suppressed. The resin member can be produced at lower cost.

In this case, when the resin member is immersed in a physiological saline for 60 minutes, it is preferable that the amount of metal ion of the antiviral agent to be eluted from the surface portion of the resin member fall within a range of 0.1 mg/m$^2$ or more and 100 mg/m$^2$ or less. When the elution amount is less than 0.1 mg/m$^2$, the antiviral effect is low. When it is more than 100 mg/m$^2$, the antiviral effect is not very different from that when it is 100 mg/m$^2$ or less. The elution amount used herein represents an amount of metal ion of the antiviral agent to be eluted per unit surface area of exhibiting the antiviral effect.

A method for measuring the elution amount is as follows. An antiviral resin member as a sample is immersed in a physiological saline for 60 minutes. Subsequently, the amount of metal ion eluted is quantitatively determined, and the elution amount per unit area of immersed surface is calculated.

When the surface potential-controlling agent 30 is contained in a resin, the surface potential-controlling agent 30 controls the surface potential of the resin to a value on the positive side of the surface potential of a resin alone. The surface potential-controlling agent 30 of the embodiment is not particularly limited as long as it causes the surface potential of the resin to shift positively, and a cationic surfactant is preferably used.

The surface potential of a resin is generally negative. Since the surface potential of viruses is negative regardless of the genome type or the presence of an envelope, the viruses are hard to adsorb to the surface of the resin. Therefore, even when only the antiviral agent is contained in the resin, the antiviral effect is hard to be exhibited. When the surface potential-controlling agent 30 is contained in the resin 10, the surface potential of the resin 10 is controlled positively. Thus, viruses easily adsorb to the resin 10 (antiviral resin member 1). Accordingly, the antiviral effect due to the antiviral agent 20 can be effectively exhibited.

In the embodiment, a cationic surfactant can be used as the surface potential-controlling agent 30. Examples of the cationic surfactant may include a quaternary ammonium salt-type cationic surfactant including a tetraalkyl ammonium salt (having 4 to 100 carbon atoms (hereinafter also referred to as Cn (wherein n is a positive integer)) (for example, lauryl trimethyl ammonium chloride, didecyl dimethyl ammonium chloride, dioctyl dimethyl ammonium bromide, and stearyl trimethyl ammonium bromide), a (C3 to C80) trialkyl benzyl ammonium salt (for example, lauryl dimethyl benzyl ammonium chloride), a (C2 to C60) alkyl pyridinium salt (for example, cetyl pyridinium chloride), a (C2 to C4) polyoxyalkylene trialkyl ammonium salt (for example, polyoxyethylene trimethyl ammonium chloride), and a sapamine type quaternary ammonium salt (for example, stearamide ethyldiethylmethyl ammonium methosulfate), and an amine salt-type cationic surfactant including salts of inorganic acids (for example, hydrochloric acid, sulfuric acid, nitric acid, and phosphoric acid) or (C2 to C22) organic acids (for example, acetic acid, propionic acid, lauric acid, oleic acid, benzoic acid, succinic acid, adipic acid, and azelaic acid) of a higher aliphatic amine (C12 to C60, for example, laurylamine, stearylamine, cetylamine, hydrogenated beef tallow amine, and rosin amine), salts of inorganic acids (for example, hydrochloric acid, sulfuric acid, nitric acid, and phosphoric acid) or (C2 to C22) organic acids (for example, acetic acid, propionic acid, lauric acid, oleic acid, benzoic acid, succinic acid, adipic acid, and azelaic acid) of EO adducts of an aliphatic amine (C1 to C30), and salts of inorganic acids (for example, hydrochloric acid, sulfuric acid, nitric acid, and phosphoric acid) or (C2 to C22) organic acids (for example, acetic acid, propionic acid, lauric acid, oleic acid, benzoic acid, succinic acid, adipic acid, and azelaic acid) of a tertiary amine (C3 to C30, for example, triethanolamine monostearate and stearamide ethyldiethylmethyl ethanol amine).

In the embodiment, the state and shape of the surface potential-controlling agent are not particularly limited and can be appropriately set by those skilled in the art. However, a liquid surface potential-controlling agent is contained in the resin to cause bubbling or the like. Therefore, a solid surface potential-controlling agent is preferred.

In the embodiment, the contained amount of the surface potential-controlling agent is not particularly limited and can be appropriately set by those skilled in the art. It is preferable that the contained amount fall within a range of 0.01% by mass or more and 10.0% by mass or less. When the contained amount is less than 0.01% by mass, the surface potential of the resin cannot be sufficiently shifted. When it is more than 10.0% by mass, the resin has tackiness on the surface.

Furthermore, in the embodiment of the present invention, the antiviral resin member 1 may contain any functional material to impart a desired function to the resin 10, in addition to the antiviral agent 20 and the surface potential-controlling agent 30. Examples of the functional material may include an antimicrobial agent, a mildewproofing agent, and a catalyst.

A method for producing the antiviral resin member 1 will be described more specifically.

A method for producing an antiviral resin member rationally at low cost is as follows. Master batch pellets that are pellets made of a resin containing a high concentration of antiviral agent are produced in advance, and are mixed with a surface potential-controlling agent and resin pellets in a certain ratio. Furthermore, the mixture is melted and kneaded to produce an antiviral resin member.

A commercially available antiviral agent is milled into nano-scale particles by a jet mill, a hammer mill, a ball mill, a vibration mill, or a bead mill. A milling method is not particularly limited, and dry and wet milling can be used. When particles having a diameter of 3 μm or less are used as an antiviral agent, a milling process may not be necessarily performed. Furthermore, an antiviral agent may be synthesized to obtain nano-scale particles. In this case, the milling process is not necessary.

In a method for producing the master batch pellets, an antiviral agent is first mixed with commercially available resin pellets. The antiviral agent is uniformly contained in the resin by a kneading extruder. The mixture is cooled, and finely cut by a pelletizer to obtain master batch pellets containing the antiviral agent in a high concentration.

The master batch pellets containing a high concentration of antiviral agent are mixed with a surface potential-controlling agent and resin pellets that are the same as the above-described resin pellets in a certain ratio. The mixture is melted and kneaded, and molded by a molding apparatus, to obtain an antiviral resin member 1 in which the antiviral agent and the surface potential-controlling agent are uniformly dispersed in the resin.

At a stage of producing the master batch pellets, the surface potential-controlling agent may be added together with the antiviral agent, to obtain master batch pellets containing the surface potential-controlling agent.

Furthermore, the antiviral resin member 1 can be produced as a molded article by a process such as injection molding and blow molding.

In the present invention, the antiviral resin member 1 includes an antiviral resin member formed by a molding treatment such as injection molding and blow molding, as well as film-shaped, fibrous, cloth-shaped, mesh-shaped, honeycomb-shaped, and nonwoven fabric-shaped members, for example. In addition to the antiviral resin member formed in a predetermined shape, film-shaped and fibrous antiviral resin members are also referred to as a molded body in this description. Furthermore, the production of the antiviral resin members is referred to as molding. The antiviral resin member 1 of the present invention can be produced in various structures (shape, size, etc.) according to the intended use. The antiviral resin member 1 can be produced as a sheet or a film by a T-die method, an inflation method, or the like. Furthermore, the antiviral resin member 1 can be produced as a filament (fiber) by a melt-spinning method or the like. Moreover, the antiviral resin member 1 can be produced as a nonwoven fabric by known production methods such as a spun-bond method.

Figure 2:
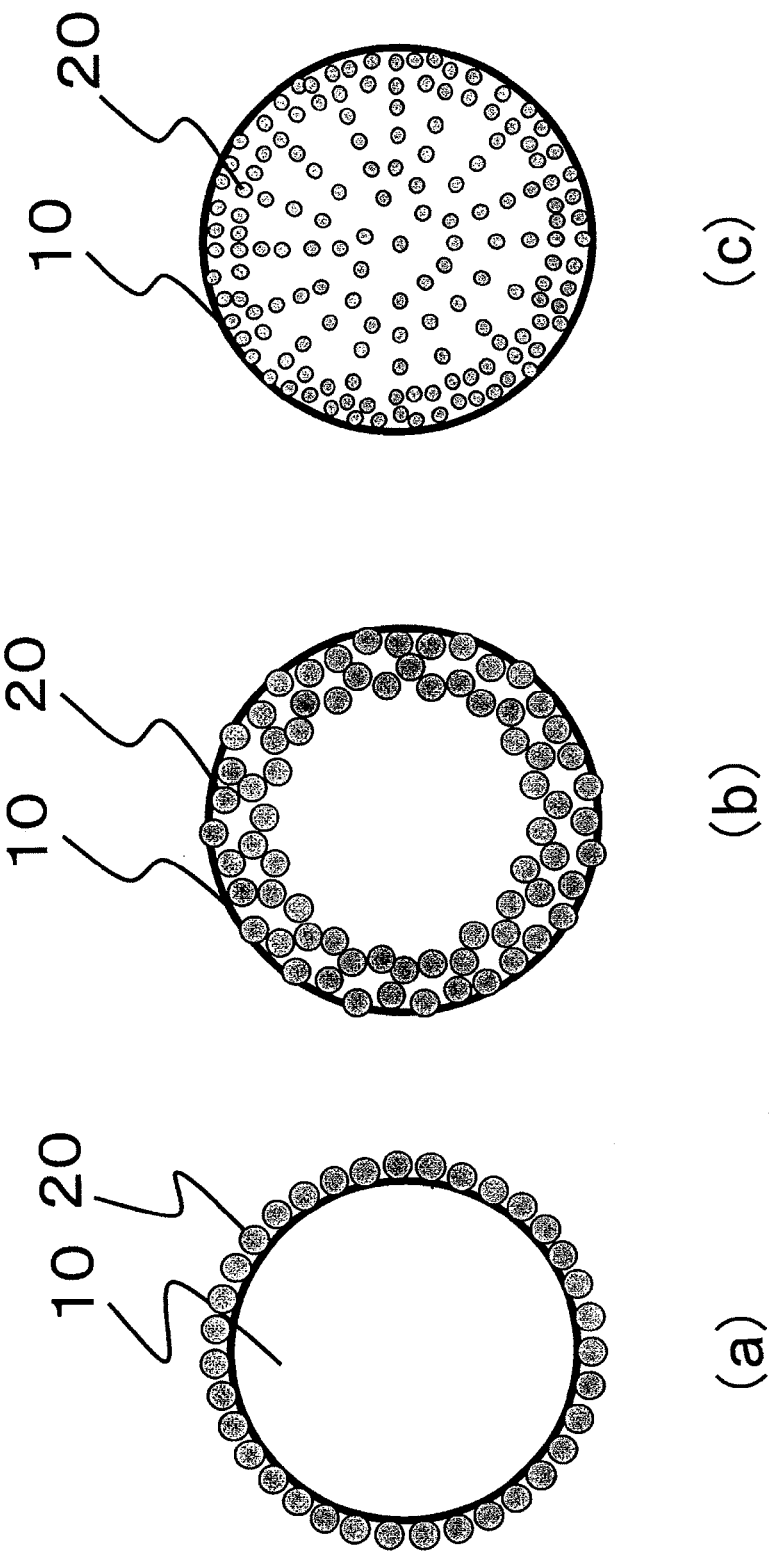
FIG. 2 is a view illustrating appearances in which a precipitation state of an antiviral agent is changed when the time and amount to be impregnated with ions of a monovalent copper compound and/or an iodide are changed.

Next, another method for producing the antiviral resin member 1 in the present invention will be described. Only the resin 10 is produced in a structure according to the intended use. The resin may be impregnated with a monovalent copper compound and/or an iodide in a state of ions as the antiviral agent 20, to precipitate the monovalent copper compound and/or the iodide inside the resin 10. A portion where the antiviral agent 20 is present can be controlled by the time and amount to be impregnated with the ions of the monovalent copper compound and/or the iodide. FIG. 2 is a view illustrating appearances in which the precipitation state of the antiviral agent 20 is changed when the time and amount impregnated with ions of the monovalent copper compound and/or the iodide are changed. In FIG. 2, the resin 10 is a granulated substance, and the cross section thereof is schematically shown. FIG. 2 shows three kinds of (a) a state in which the antiviral agent 20 is present at the surface of the resin 10, (b) a state in which the antiviral agent 20 is present at the surface portion, and (c) a state in which the antiviral agent 20 is present at the surface portion and the inside of the resin 10.

The heating and stretching process will next be described. The heating and stretching process is a process of heating and stretching the antiviral resin member 1 molded by the above-described method. In particular, the antiviral resin member 1 that is a fibrous, sheet-shaped, or film-shaped molded body can be subjected to the heating and stretching process to easily improve the antiviral properties. The heating and stretching process may include a plurality of stretching steps. When the heating and stretching process includes a plurality of stretching steps, a product of stretch ratios in the respective stretching steps means a total stretch ratio. When the heating and stretching process includes one stretching step, the stretch ratio in the stretching step means a total stretch ratio.

A stretching method is also not particularly limited. Any known stretching method such as a hot roll stretching method, a hot plate stretching method, a tubular stretching method, a stretch blow method, and a laser stretching method may be used. The antiviral resin member is heated and stretched to obtain a higher antiviral effect.

For example, another stretching method is a biaxial stretch blow molding method of a molded body. A preform formed previously by injection molding is stretched in two directions with high stretch ratio, or longitudinal and transverse directions, and the preform is molded by blowing high-pressure air. Thus, a high antiviral effect is achieved.

For example, when a film formed by the T-die method or the inflation method is used as the antiviral resin member 1, the film may then be stretched uniaxially or biaxially. This is a treatment in which the film is stretched in a certain direction under heating. When a film is formed by the T-die method or the inflation method as the antiviral resin member 1, a higher antiviral effect is achieved by the stretching step. In the T-die method, a film is stretched by a flat stretching method. Specifically, a film is stretched in a film traveling direction (longitudinal direction) by a difference of rotational speed between rolling rollers. The film is gripped by a clip and extended in a transverse direction. Furthermore, the stretching method includes sequential biaxial stretching including stretching in a longitudinal direction followed by stretching in a transverse direction, simultaneous biaxial stretching including stretching simultaneously in the longitudinal and transverse directions, and multistage stretching including stretching at a plurality of stages such as three stages of longitudinal, transverse, and longitudinal directions.

In the inflation method, a film is stretched by a tubular film method. A film formed by extrusion is heated by a heater for preheating as it is. At a heater portion, the film is then stretched in the longitudinal direction by a rolling speed of a roller and in the transverse direction by air pressure.

For example, the antiviral resin member 1 of the embodiment may be formed in a fibrous shape as described above, or may be formed as a filament fiber. In the filament fiber, the stretching step is generally performed after spinning, and thus the arrangement of molecules constituting the fiber is reformed. When a filament fiber obtained by spinning a polymeric material containing the antiviral agent 2 is used as the antiviral resin member 1, a higher antiviral effect is achieved by the stretching step as compared with an unstretched yarn.

The stretch ratio in the stretching step is appropriately set according to a substance to be stretched and a stretching method. The stretch ratio is generally set so that the total stretch ratio is 1.5 or more and 10.0 or less. When the stretch ratio is less than 1.5, the antiviral effect is not largely changed. When the stretch ratio is more than 10.0, the stretching tension is extremely high. Therefore, the resin member is easily cut, and the processability may be reduced.

Currently, a mechanism in which the antiviral effect is largely improved by stretching is not completely clear. For example, when the antiviral resin member 1 is fibrous, the resin in a melting state is cooled and solidified at a cooling and solidification stage in a spinning process. Therefore, the cooling speeds at the surface portion (skin layer) and an inner layer portion near to a core (core layer) are different. From a difference of the cooling speed, it is considered that a fibrous structure formed in the surface portion is different from a structure of the fibrous inner layer portion. During heating and stretching in this situation, stretching is performed under a heating condition that is equal to or higher than the glass transition point. As a result, the structure of the surface portion that is different from the inner layer portion is transformed into a structure in which the difference between the structure of the surface portion and that of the inner layer portion is reduced by heating and stretching, resulting in a structure in which virus inactivation fine particles easily come into contact with a moisture content. The transformation of the structure affects charge at the surface of viruses, DNA, or the like, to inactivate the viruses. This is applicable to the sheet-shaped and film-shaped antiviral resin members 1 other than the fibrous antiviral resin member.

The antiviral resin member 1 of the embodiment can be applied to fibers and products having a fibrous structure including agricultural materials such as a greenhouse film and a tunnel greenhouse film, stationeries such as a clear folder and a labeled tape, a seat, a chair, a couch, building materials such as an external wall material, a window frame, a door, a window shade, a ceiling, a floor panel, and a window, interior materials such as a wallpaper, a carpet rag, and a resin tile, interior materials for vehicle, clothes, innerwear, stockings, gloves, footwear such as shoe covers and shoes, bedding materials such as a pajama, a mat, a sheet, a pillow, a pillowcase, a blanket, a towel blanket, a futon, and a cover for a futon, a cap, a handkerchief, a towel, a carpet, a curtain, filters for an air cleaner, an air conditioner, a ventilator, a vacuum cleaner, and a fan, fishnets such as a well and a fixed net, a filter for a water treatment, a filter for potable water, a filter for a ballast water treatment, a pipe lining material, a film-shaped member that is attached to the surface of a coastal structure through an adhesive or a tacking agent, a sheet-shaped member that adheres to the surface of a ship such as a fishing boat and a tanker, various members in contact with water such as a sheet-shaped member used for an inner wall of a water intake opening, a pre-filter for a water intake opening, an inner face of a water intake opening, a plate air conditioner, a drainage pipe, and a feed pipe, that are used in an electric power plant, a mosquito net, and a mesh for screen printing. Therefore, the member of the present invention is useful in providing excellent various products in a variety of fields.

EXAMPLES

The present invention will next be described more specifically with reference to Examples. However, the present invention is not limited to these Examples.
(Production of Antiviral Injection Molding Member)

Example 1

A commercially available copper (I) iodide powder (available from Nihon Kagaku Sangyo Co., Ltd.) was dry milled to obtain copper iodide fine particles having an average particle diameter of 150 nm.
Polyethylene resin pellets (available from Asahi Kasei Chemicals Corporation) as a base resin were added so that the amount of the copper iodide was 42% by mass, the mixture was supplied to a biaxial melting kneader, and master batch pellets were obtained.
Polyethylene resin pellets, the master batch pellets, and a cationic surfactant (available from Lion Corporation, ARQUAD 22-80) were mixed so that the amounts of the copper iodide and the cationic surfactant were 3% by mass and 0.5% by mass, respectively. The mixture was injection molded by an injection molding apparatus to obtain an antiviral resin member as a molded body.

Example 2

An antiviral molded member was obtained in the same condition as in Example 1 except that the polyethylene resin pellets, the master batch pellets, and the cationic surfactant were mixed so that the contents of the copper iodide and the cationic surfactant in the antiviral resin member were 6% by mass and 1% by mass, respectively.

Example 3

An antiviral resin member was obtained in the same condition as in Example 1 except that a cationic surfactant (available from Lion Corporation, ARQUAD 2HP FLAKE) was used instead of the cationic surfactant used in Example 1 and the polyethylene resin pellets, the master batch pellets, and the cationic surfactant were mixed so that the amounts of the copper iodide and the cationic surfactant in the antiviral resin member were 3% by mass and 0.1% by mass, respectively.

Example 4

An antiviral resin member was obtained in the same condition as in Example 3 except that the polyethylene resin pellets, the master batch pellets, and the cationic surfactant were mixed so that the amounts of the copper iodide and the cationic surfactant in the antiviral resin member were 6% by mass and 0.5% by mass, respectively.

Example 5

An antiviral resin member was obtained in the same condition as in Example 1 except that a cationic surfactant (available from Lion Corporation, ARMAC HT FLAKE) was used instead of the cationic surfactant used in Example 1 and the polyethylene resin pellets, the master batch pellets, and the cationic surfactant were mixed so that the amounts of the copper iodide and the cationic surfactant in the antiviral resin member were 3% by mass and 1% by mass, respectively.

Example 6

An antiviral resin member was obtained in the same condition as in Example 5 except that the polyethylene resin pellets, the master batch pellets, and the cationic surfactant were mixed so that the amounts of the copper iodide and the cationic surfactant in the antiviral resin member were 6% by mass and 0.1% by mass, respectively.

Example 7

A commercially available silver (I) iodide powder (available from Wako Pure Chemical Industries, Ltd., for chemistry) as an antiviral agent was dry milled to obtain silver iodide fine particles having an average particle diameter of 1.6 μm.
Polyethylene resin pellets (available from Asahi Kasei Chemicals Corporation) as a base resin were added so that the amount of the silver iodide was 30% by mass, the mixture was supplied to a biaxial melting kneader, and master batch pellets were obtained.
Polyethylene resin pellets, the master batch pellets, and a cationic surfactant (available from Lion Corporation, ARQUAD 22-80) were mixed so that the amounts of the silver iodide and the cationic surfactant were 10% by mass and 5% by mass, respectively. The mixture was injection molded by an injection molding apparatus to obtain an antiviral resin member as a molded body.

Example 8

An antiviral molded member was obtained in the same condition as in Example 7 except that the polyethylene resin pellets, the master batch pellets, and the cationic surfactant were mixed so that the amounts of the silver iodide and the cationic surfactant in the antiviral resin member were 20% by mass and 2% by mass, respectively.

Example 9

A commercially available copper (I) chloride powder (available from Wako Pure Chemical Industries, Ltd., Wako 1st Grade) was dry milled to obtain copper chloride fine particles having an average particle diameter of 150 nm.
Polyethylene resin pellets (available from Asahi Kasei Chemicals Corporation) as a base resin were added so that the amount of the copper chloride was 50% by mass, the mixture was supplied to a biaxial melting kneader, and master batch pellets were obtained.

Polyethylene resin pellets, the master batch pellets, and a cationic surfactant (available from Lion Corporation, ARQUAD 22-80) were mixed so that the amounts of the copper chloride and the cationic surfactant were 30% by mass and 1% by mass, respectively. The mixture was injection molded by an injection molding apparatus to obtain an antiviral resin member as a molded body.

Example 10

An antiviral molded member was obtained in the same condition as in Example 9 except that the polyethylene resin pellets, the master batch pellets, and the cationic surfactant were mixed so that the amounts of the copper chloride and the cationic surfactant in the antiviral resin member were 40% by mass and 0.01% by mass, respectively.

Example 11

A commercially available copper (I) oxide powder (available from Wako Pure Chemical Industries, Ltd., Wako 1st Grade) was dry milled to obtain silver iodide fine particles having an average particle diameter of 400 nm.

Polyethylene resin pellets (available from Asahi Kasei Chemicals Corporation) as a base resin were added so that the amount of the copper oxide was 30% by mass, the mixture was supplied to a biaxial melting kneader, and master batch pellets were obtained.

Polyethylene resin pellets, the master batch pellets, and a cationic surfactant (available from Lion Corporation, ARQUAD 22-80) were mixed so that the amounts of the copper oxide and the cationic surfactant were 0.5% by mass and 10% by mass, respectively. The mixture was injection molded by an injection molding apparatus to obtain an antiviral resin member as a molded body.

Example 12

An antiviral resin member was obtained in the same condition as in Example 11 except that the polyethylene resin pellets, the master batch pellets, and the cationic surfactant were mixed so that the amounts of the copper oxide and the cationic surfactant in the antiviral resin member were 5% by mass and 3% by mass, respectively.

Comparative Example 1

Polyethylene resin pellets were molded by an injection molding apparatus without copper iodide and a surfactant to obtain an injection molded member.

Comparative Example 2

An antiviral resin member was obtained in the same condition as in Example 1 except that the polyethylene resin pellets and the master batch pellets were mixed without a surfactant so that the amount of the copper iodide in the antiviral resin member was 3% by mass.

Comparative Example 3

An antiviral resin member was obtained in the same condition as in Comparative Example 1 except that the polyethylene resin pellets and a cationic surfactant (available from Lion Corporation, ARQUAD 22-80) were mixed without copper iodide so that the amount of the cationic surfactant in the antiviral resin member was 0.5% by mass.

Comparative Example 4

An antiviral resin member was obtained in the same condition as in Comparative Example 3 except that the polyethylene resin pellets and a cationic surfactant (available from Lion Corporation, ARQUAD 2HP FLAKE) were mixed without copper iodide so that the amount of the cationic surfactant in the antiviral resin member was 0.5% by mass.

Comparative Example 5

An antiviral resin member was obtained in the same condition as in Comparative Example 3 except that polyethylene resin pellets and a cationic surfactant (available from Lion Corporation, ARMAC HT FLAKE) were mixed without copper iodide so that the amount of the cationic surfactant in the antiviral resin member was 0.5% by mass.

Comparative Example 6

An antiviral resin member was obtained in the same condition as in Example 1 except that a nonionic surfactant (available from Lion Corporation, ELECTROSTRIPPER TS-3B) was used instead of the cationic surfactant used in Example 1 and the polyethylene resin pellets, the master batch pellets, and the cationic surfactant were mixed so that the amounts of the copper iodide and the nonionic surfactant in the antiviral resin member were 3% by mass and 0.5% by mass, respectively.

Comparative Example 7

An antiviral resin member was obtained in the same condition as in Example 1 except that an anionic surfactant (available from Tayca Corporation, TAYCAPOWER LN2450) was used instead of the cationic surfactant used in Example 1 and the polyethylene resin pellets, the master batch pellets, and the cationic surfactant were mixed so that the amounts of the copper iodide and the anionic surfactant in the antiviral resin member were 3% by mass and 0.5% by mass, respectively.

The compositions of the molded members in Examples 1 to 6 and Comparative Examples 1 to 7 as described above are shown in Table 1.

TABLE 1

| | ANTIVIRAL AGENT | | SURFACTANT | |
|---|---|---|---|---|
| | TYPE | % BY MASS | TYPE/TRADE NAME | % BY MASS |
| Example 1 | CuI | 3 | CATIONIC/ARQUAD 22-80 | 0.5 |
| Example 2 | CuI | 6 | CATIONIC/ARQUAD 22-80 | 1 |
| Example 3 | CuI | 3 | CATIONIC/ARQUAD 2HP FLAKE | 0.1 |
| Example 4 | CuI | 6 | CATIONIC/ARQUAD 2HP FLAKE | 0.5 |

TABLE 1-continued

| | ANTIVIRAL AGENT | | SURFACTANT | |
|---|---|---|---|---|
| | TYPE | % BY MASS | TYPE/TRADE NAME | % BY MASS |
| Example 5 | CuI | 3 | CATIONIC/ARMAC HT FLAKE | 1 |
| Example 6 | CuI | 6 | CATIONIC/ARMAC HT FLAKE | 0.1 |
| Example 7 | AgI | 10 | CATIONIC/ARQUAD 22-80 | 5 |
| Example 8 | AgI | 20 | CATIONIC/ARQUAD 22-80 | 2 |
| Example 9 | CuCl | 30 | CATIONIC/ARQUAD 22-80 | 1 |
| Example 10 | CuCl | 40 | CATIONIC/ARQUAD 22-80 | 0.01 |
| Example 11 | $Cu_2O$ | 0.5 | CATIONIC/ARMAC HT FLAKE | 10 |
| Example 12 | $Cu_2O$ | 5 | CATIONIC/ARMAC HT FLAKE | 3 |
| Comparative Example 1 | — | — | — | — |
| Comparative Example 2 | CuI | 3 | — | — |
| Comparative Example 3 | — | — | CATIONIC/ARQUAD 22-80 | 0.5 |
| Comparative Example 4 | — | — | CATIONIC/ARQUAD 2HP FLAKE | 0.5 |
| Comparative Example 5 | — | — | CATIONIC/ARMAC HT FLAKE | 0.5 |
| Comparative Example 6 | CuI | 3 | NONIONIC/ELECTROSTRIPPER TS-3B | 0.5 |
| Comparative Example 7 | CuI | 3 | ANIONIC/TAYCAPOWER LN2450 | 0.5 |

(Production of Antiviral Sheet Member)

Example 13

A commercially available copper (I) iodide powder (available from Nihon Kagaku Sangyo Co., Ltd.) was dry milled to obtain copper iodide fine particles having an average particle diameter of 120 nm.
Polyethylene resin pellets (available from Asahi Kasei Chemicals Corporation) as a base resin were added so that the amount of the copper iodide was 42% by mass, the mixture was supplied to a biaxial melting kneader, and master batch pellets were obtained.
Polyethylene resin pellets, the master batch pellets, and a cationic surfactant (available from Lion Corporation, ARQUAD 2HP FLAKE) were mixed so that the amounts of the copper iodide and the cationic surfactant were 3% by mass and 0.1% by mass, respectively. The mixture was molded by a T-die extruder to obtain a sheet-shaped antiviral resin member having a thickness of 50 μm.

Example 14

A sheet-shaped antiviral resin member was obtained in the same condition as in Example 13 except that the polyethylene resin pellets, the master batch pellets, and the cationic surfactant were mixed so that the amounts of the copper iodide and the cationic surfactant in the sheet-shaped member were 5% by mass and 0.1% by mass, respectively.

Example 15

A sheet-shaped antiviral resin member was obtained in the same condition as in Example 13 except that polypropylene resin pellets (available from Japan Polypropylene Corporation) were used instead of the polyethylene resin pellets used in Example 13 and the thickness of the member was 300 μm.

Example 16

A sheet-shaped antiviral resin member was obtained in the same condition as in Example 15 except that the polypropylene resin pellets, the master batch pellets, and the cationic surfactant were mixed so that the amounts of the copper iodide and the cationic surfactant in the sheet-shaped molded member were 5% by mass and 0.1% by mass, respectively.

Example 17

The sheet-shaped resin member obtained in Example 13 was biaxially stretched at a stretch ratio of 1.5 by a tenter to obtain a sheet-shaped antiviral resin member.

Example 18

The sheet-shaped resin member obtained in Example 15 was biaxially stretched at a stretch ratio of 10 by a tenter to obtain a sheet-shaped antiviral resin member.

Example 19

A sheet-shaped antiviral resin member was obtained in the same condition as in Example 13 except that the polyethylene resin pellets, the master batch pellets, and the cationic surfactant were mixed so that the amounts of the copper iodide and the cationic surfactant in the sheet-shaped molded member were 0.3% by mass and 0.1% by mass, respectively.

Comparative Example 8

Polyethylene resin pellets were molded by a T-die extruder without copper iodide and a surfactant to obtain a sheet-shaped resin member having a thickness of 50 μm.

Comparative Example 9

Polypropylene resin pellets were molded by a T-die extruder without copper iodide and a surfactant to obtain a sheet-shaped resin member having a thickness of 300 μm.
The compositions of the sheet-shaped resin members in Examples 13 to 19 and Comparative Examples 8 and 9 as described above are summarized in Table 2.

TABLE 2

| | RESIN | ANTI-VIRAL AGENT (% by mass) | SURFACE POTENTIAL-CONTROLLING AGENT (% by mass) | STRETCH RATIO (FOLD) |
|---|---|---|---|---|
| Example 13 | POLYETHYLENE | 3 | 0.1 | 0 |
| Example 14 | POLYETHYLENE | 5 | 0.1 | 0 |
| Example 15 | POLYPROPYLENE | 3 | 0.1 | 0 |
| Example 16 | POLYPROPYLENE | 5 | 0.1 | 0 |
| Example 17 | POLYETHYLENE | 3 | 0.1 | 1.5 |
| Example 18 | POLYPROPYLENE | 3 | 0.1 | 10 |
| Example 19 | POLYETHYLENE | 0.3 | 0.1 | 0 |
| Comparative Example 8 | POLYETHYLENE | — | — | 0 |
| Comparative Example 9 | POLYPROPYLENE | — | — | 0 |

(Production of Antiviral Fibers)

Example 20

A commercially available copper (I) iodide powder (available from Nihon Kagaku Sangyo Co., Ltd.) was dry milled to obtain copper iodide fine particles having an average particle diameter of 150 nm.

A polyester resin (available from UNITIKA LTD.) as a base resin was added so that the amount of the copper iodide was 20% by mass, the mixture was supplied to a biaxial melting kneader, and master batch pellets were obtained.

Polyethylene resin pellets, the master batch pellets, and a cationic surfactant (available from Lion Corporation, ARQUAD 22-80) were mixed so that the amounts of the copper iodide and the cationic surfactant were 3% by mass and 0.1% by mass, respectively. The mixture was melt spun by a monofilament spinning apparatus (manufactured by Chubu Kagaku Kikai Seisakusho K.K.), passed through a water tank at 60° C., and then was cooled and solidified to produce a polyester monofilament having a fiber diameter of 300 μm. The polyester monofilament was wound at a spinning speed of 20 m/min. The wound fiber passed through a wet stretching apparatus capable of heating by vapor at a stretching temperature of 100° C., a delivery speed of 20 m/min, and a winding speed of 70 m/min. Thus, the fiber was stretched 3.5 times to obtain an antiviral resin fiber having a diameter of 100 μm.

Comparative Example 10

A resin fiber was obtained in the same condition as in Example 20 except that the master batch pellets and the cationic surfactant were not mixed and an antiviral agent was not used.

The compositions of the resin fibers in Example 20 and Comparative Example 10 as described above are shown in Table 3.

TABLE 3

| | RESIN | ANTI-VIRAL AGENT (% by mass) | SURFACE POTENTIAL-CONTROLLING AGENT (% by mass) | STRETCH RATIO (FOLD) |
|---|---|---|---|---|
| Example 20 | POLYESTER | 3 | 0.1 | 3.5 |
| Comparative Example 10 | POLYESTER | — | — | 3.5 |

(Evaluation Method of Antiviral Properties)

An influenza virus (influenza A/Kita Kyushu/159/93 (H3N2)) cultured using MDCK cells was used as a virus with an envelope in the measurement of virus inactivation of a resin member. In addition, a feline calicivirus generally used as a substitute for a norovirus was used as a virus having no envelope.

(Sheet-shaped Injection Molded Member)

The sheet-shaped injection molded member (20 mm×20 mm) in each of Examples and Comparative Examples was placed in a plastic petri dish. To the member, 25 μL of viral solution was added dropwise and the reaction was held at room temperature for 60 minutes. At this time, the upper surface of the specimen of the resin member was covered with a PP film (20 mm×20 mm). While a contact area between the viral solution and the specimen was kept constant, a test was performed. After the reaction for 60 minutes, 975 μL of SCDLP broth was added to stop the reaction. The viruses were washed off by pipetting. Each of the viral solutions after the reaction was diluted with an MEM diluent to $10^{-2}$ to $10^{-5}$ (10-fold serial dilution), to obtain a sample solution. 100 μL of the sample solution was inoculated into MDCK cells cultured in a petri dish, and allowed to stand for 60 minutes to allow the viruses to adsorb the cells. After that, the cells were overlaid with a 0.7% agar medium, and cultured in a 5% $CO_2$ incubator at 34° C. for 48 hours. The number of formed plaques was counted to calculate the infectivity titer (PFU/0.1 mL, log 10); (PFU: plaque forming units) of the viruses after formalin fixation and methylene blue staining.

(Fibers)

The fibers (amount set so that the surface area of fibers was 400 mm²) in each of Example 20 and Comparative Example 10 were placed in a 1.5-mL sterile tube. To the fibers, 200 μL of viral solution was added dropwise and the reaction was held at room temperature for 60 minutes. After the reaction for 60 minutes, 1,800 μL of SCDLP broth was added. The viruses were washed off by vortexing. Each viral solution after the reaction was diluted with an MEM diluent to $10^{-2}$ to $10^{-5}$ (10-fold serial dilution). 100 μL of sample solution was inoculated into MDCK cells cultured in a petri dish, and allowed to stand for 60 minutes to allow the viruses to adsorb the cells. After that, the cells were overlaid with a 0.7% agar medium, and cultured in a 5% $CO_2$ incubator at 34° C. for 48 hours. The number of formed plaques was counted to calculate the infectivity titer (PFU/0.1 mL, log 10); (PFU: plaque forming units) of the virus after formalin fixation and methylene blue staining.

(Evaluation Method of Surface Potential)

The resin member in each of Examples and Comparative Examples was cut into a size of 10 mm×25 mm, and the surface potential was measured by a zeta potential measurement system (manufactured by Otsuka Electronics Co., Ltd., ELSZ-1).

(Measurement Method of Elution Amount)

The sheet-shaped member (40 mm×40 mm) in each of Examples and Comparative Examples was placed in a 5-mL tube, and immersed in 4 mL of physiological saline for 60 minutes. After the immersion for 60 minutes, the amount of copper ion eluted in the physiological saline was determined by an atomic absorption spectrophotometer (manufactured by Hitachi High-Technologies Corporation). Subsequently, the elution amount per unit surface area of the immersed member was calculated.

The measurement results of the antiviral resin members as the molded members in Examples 1 to 12 and Comparative Examples 1 to 7 as described above are summarized in Table 4.

TABLE 4

| | INFLUENZA VIRUS INFECTIVITY TITER (PFU/0.1 ml, Log10) | FELINE CALICIVIRUS INFECTIVITY TITER (PFU/0.1 ml, Log10) | SURFACE POTENTIAL (mV) | METAL ION ELUTION AMOUNT (mg/m$^2$) |
|---|---|---|---|---|
| Example 1 | 3.43 | <1.60 | 11.60 | — |
| Example 2 | <1.60 | <1.60 | 17.88 | — |
| Example 3 | 3.00 | — | −0.24 | — |
| Example 4 | <1.60 | <1.60 | 24.64 | — |
| Example 5 | <1.60 | — | 48.49 | — |
| Example 6 | <1.60 | 2.34 | 44.61 | — |
| Example 7 | 2.00 | 2.20 | — | 12 |
| Example 8 | <1.60 | <1.60 | — | 25 |
| Example 9 | <1.60 | <1.60 | — | 34 |
| Example 10 | <1.60 | <1.60 | 1.26 | 46 |
| Example 11 | 1.8 | 2.00 | 88.34 | 0.13 |
| Example 12 | <1.60 | 1.70 | — | 1.42 |
| Comparative Example 1 | 4.73 | 5.00 | −26.54 | — |
| Comparative Example 2 | 4.72 | 5.40 | −23.37 | — |
| Comparative Example 3 | 4.59 | 5.24 | 11.96 | — |
| Comparative Example 4 | 4.59 | — | 37.05 | — |
| Comparative Example 5 | 3.53 | 4.30 | 54.26 | — |
| Comparative Example 6 | 2.43 | 5.53 | −32.10 | — |
| Comparative Example 7 | 3.80 | 5.33 | −47.25 | — |
| VIRUS CONTROL | 5.56 | 6.17 | — | — |

NOTE 1:
"<1.60" IN TABLE REPRESENTS NOT MORE THAN LOWER LIMIT OF INFECTIVITY TITER MEASUREMENT.

As confirmed from the results of the resin members in Table 4, the infectivity titers of an influenza virus with an envelope in all Examples 1 to 12 are decreased. From comparison with Examples 1 to 12 and Comparative Examples 1 to 7, it is confirmed that the antiviral properties are not exhibited by the absence of both the antiviral agent and the cationic surfactant. Furthermore, it is confirmed that the surface potentials in Examples 1 to 6, 10, and 11 are shifted more positively than that of a resin member alone (Comparative Examples 1 and 2) that does not contain a surfactant since the cationic surfactant is contained.

In Comparative Examples 6 and 7, a nonionic or anionic surfactant is contained, but the surface potential is not shifted positively. Furthermore, in Comparative Examples 6 and 7, the infectivity titers of an influenza virus (with an envelope) are decreased, and the infectivity titers of a feline calicivirus (having no envelope) are not decreased when compared with those in Comparative Examples 1 and 2 in which a surfactant is not contained.

It is considered that the infectivity titer of an influenza virus is decreased by nonionic and anionic surfactants. However, the effect achieved by the nonionic and anionic surfactants are lower than the effect achieved by a cationic surfactant. In addition, it is confirmed that the effect is not achieved by a feline calicivirus having no envelope. In contrast, it is confirmed that the members in Examples 1, 2, 4, and 6 to 12 can effectively inactivate a feline calicivirus having no envelope.

The measurement results of the antiviral resin members as the sheet members in Examples 13 to 19 and Comparative Examples 8 and 9 are summarized in Table 5.

TABLE 5

| | INFLUENZA VIRUS INFECTIVITY TITER (PFU/0.1 ml, Log10) | SURFACE POTENTIAL (mV) | METAL ION ELUTION AMOUNT (mg/m$^2$) |
|---|---|---|---|
| Example 13 | 3.17 | −15.68 | 0.52 |
| Example 14 | 2.30 | −7.42 | 1.26 |
| Example 15 | 3.21 | −14.65 | 0.32 |
| Example 16 | 2.20 | −23.37 | 0.50 |
| Example 17 | <1.60 | — | 2.20 |
| Example 18 | <1.60 | — | 3.00 |
| Example 19 | 3.97 | — | 0.08 |
| Comparative Example 8 | 5.18 | −45.87 | 0.00 |
| Comparative Example 9 | 5.23 | −56.63 | 0.00 |
| VIRUS CONTROL | 5.24 | — | — |

As confirmed from the results of the sheet-shaped resin members in Table 5, in Examples 13 to 19, the infectivity titers are decreased more than those in Comparative Examples 8 and 9, and the surface potential is shifted positively. In Example 19 in which the contained amount of the antiviral agent is less than the preferable range, the infectivity titer is higher than those in other Examples in which the contained amount falls within the preferable range, and the elution amount of metal ion is less than the preferable range.

The measurement results of the fibrous antiviral resin members in Example 20 and Comparative Example 10 are summarized in Table 6.

TABLE 6

| | INFLUENZA VIRUS INFECTIVITY TITER (PFU/0.1 ml, Log10) | FELINE CALICIVIRUS INFECTIVITY TITER (PFU/0.1 ml, Log10) |
|---|---|---|
| Example 20 | <1.00 | <1.00 |
| Comparative Example 10 | 5.21 | 5.97 |

As confirmed from the results of the fibrous resin members in Table 6, in Example 20, the infectivity titer is decreased more than that in Comparative Example 10, and the surface potential is shifted positively.

Therefore, the antiviral effect is confirmed regardless the type of resin. From Tables 4, 5, and 6, it is confirmed that the resin members of the present invention exhibit the antiviral effect regardless of the structure.

Accordingly, the antiviral properties of the antiviral resin members obtained in the present invention are confirmed.

REFERENCE SIGNS LIST

10: Resin
20: Antiviral agent
30: Surface potential-controlling agent

The invention claimed is:

1. An antiviral resin member comprising a molded and/or solidified resin, an antiviral agent, and a surface potential-controlling agent including a cationic surfactant,
wherein:
   the surface potential-controlling agent causes the surface potential of the antiviral resin member to shift to a value on a positive side of a surface potential of the resin alone,
   the antiviral agent contains, as an active ingredient, particles of at least one monovalent copper compound,
   the antiviral agent and the surface potential-controlling agent are dispersed in the molded and/or solidified resin,
   the surface potential-controlling agent is contained in the antiviral resin member in an amount of 0.01% by mass or more and 10.0% by mass or less, and
   the antiviral agent is contained in the antiviral resin member in an amount of 0.5% by mass or more and 40% by mass or less.

2. The antiviral resin member according to claim 1, wherein the monovalent copper compound is a chloride, an acetate compound, a sulfide, an iodide, a bromide, a peroxide, an oxide, or a thiocyanide.

3. The antiviral resin member according to claim 1, wherein the antiviral resin member is a molded body obtained by molding followed by heating and stretching.

4. A method for producing an antiviral resin member comprising:
   forming a molded body from a resin, an antiviral agent, and a surface potential-controlling agent including a cationic surfactant, so that the antiviral agent and the cationic surfactant are dispersed in the resin; and
   heating and stretching the molded body,
   wherein the antiviral agent contains, as an active ingredient, particles of at least one monovalent copper compound,
   the surface potential-controlling agent is contained in the antiviral resin member in an amount of 0.01% by mass or more and 10.0% by mass or less, and
   the antiviral agent is contained in the antiviral resin member in an amount of 0.5% by mass or more and 40% by mass or less.

* * * * *